United States Patent [19]

Umezawa et al.

[11] Patent Number: 4,473,557

[45] Date of Patent: Sep. 25, 1984

[54] 3"-DEOXYSTREPTOMYCIN PRODUCTION THEREOF AND PHARMACEUTICAL COMPOSITIONS CONTAINING SAME

[75] Inventors: Hamao Umezawa; Sumio Umezawa, both of Tokyo; Tsutomu Tsuchiya; Takayuki Usui, both of Yokohama, all of Japan

[73] Assignee: Zaidan Hojin Biseibutsu Kagaku Kenkyu Kai, Tokyo, Japan

[21] Appl. No.: 475,269

[22] Filed: Mar. 9, 1983

[30] Foreign Application Priority Data

Mar. 9, 1982 [JP] Japan .................................. 57-35904

[51] Int. Cl.$^3$ ...................... A61K 31/71; C07H 15/22
[52] U.S. Cl. ..................................... 424/180; 536/14; 536/15; 536/16
[58] Field of Search ..................... 536/14, 15, 16, 13.6

[56] References Cited

U.S. PATENT DOCUMENTS

| | | | |
|---|---|---|---|
| 2,663,685 | 12/1953 | Levy | 536/15 |
| 2,790,792 | 4/1957 | Kaplan | 536/15 |
| 2,857,375 | 10/1958 | Ziegler | 536/16 |
| 4,171,356 | 10/1979 | Wright et al. | 536/13.6 |

Primary Examiner—Johnnie R. Brown
Attorney, Agent, or Firm—Sughrue, Mion, Zinn, Macpeak & Seas

[57] ABSTRACT

A new semi-synthetic antibiotic, 3"-deoxystreptomycin is now provided, which is useful as an antibacterial agent and is produced from 3"-deoxydihydrostreptomycin by a process comprising oxidizing the 3'-hydroxymethyl group of 2,5,6,4",6"-penta-O-acetyl-2"-N-benzyloxycarbonyl-3"-deoxydihydrostreptomycin as prepared by skilled introduction of amino-protecting group and hydroxyl-protecting group of appropriately selected natures into 3"-deoxydihydrostreptomycin, and then removing the protective groups from the oxidation product, 2,5,6,4",6"-penta-O-acetyl-2"-N-benzyloxycarbonyl-3"-deoxystreptomycin.

7 Claims, No Drawings

3''-DEOXYSTREPTOMYCIN PRODUCTION THEREOF AND PHARMACEUTICAL COMPOSITIONS CONTAINING SAME

SUMMARY OF THE INVENTION

This invention relates to 3''-deoxystreptomycin which is a new compound and useful as antibacterial agent. This invention also relates to a process for the production of 3''-deoxystreptomycin.

BACKGROUND OF THE INVENTION

Streptomycin is a well known antibiotic which was discovered by Wasksman. Streptomycin, and dihydrostreptomycin which is obtained by reduction of the aldehyde group of streptomycin are widely used as medicine in therapeutic treatment of bacterial infections. However, as streptomycin and dihydrostreptomycin become widely be used, such strains of bacteria resistant to these antibiotics have occurred, and owing to this the therapeutic effects of streptomycin and dihydrostreptomycin have considerably been reduced. The occurrence of such resistant bacteria is generally observed not only with the antibiotics of streptomycin type but also with other antibiotics such as kanamycins, lividomycins and the like. These historical facts are detailed in the general remarks as reported by Hamao Umezawa who is one of the present inventors and is a first discoverer of the mechanism of resistance of bacteria against aminoglycosidic antibiotics (H. Umezawa; "Advances in Carbohydrate Chemistry and Biochemistry" Vol. 30. page 183, Academic Press 1974). With the streptomycins, it has been found that the hydroxyl group at 3''-position of the molecule of streptomycins can be adenylated by such resistant bacteria capable of producing a streptomycin adenyltransferase and thereby 3''-O-adenylstreptomycins are formed, with a consequence that streptomycins can be inactivated in respect of their antibacterial effects (Umezawa et al; "Journal of Antibiotics" Vol. 21, page 81 (1968)). In these circumstances, we, the present inventiors, have started our study in an attempt to remove the 3''-hydroxyl group from the streptomycin molecule and thereby to eliminate the possibility of inactivation of streptomycin which would occur due to the adenylation of the 3''-hydroxy group of streptomycin so that there is provided a new derivative of streptomycin which will be active also against the bacteria resistant to streptomycin. As a result of our study, we succeeded in synthetizing 3''-deoxydihydrostreptomycin from streptomycin, and we found that this 3''-deoxydihydrostreptomycin is active against the resistant bacteria (see Japanese patent application prepublication "Kokai" No. 105154/77; and "Journal of Antibiotics" Vol. 29, 978 (1976)).

We have made our further study and have now succeeded in synthetically producing 3''-deoxystreptomycin with starting from the above-mentioned 3''-deoxydihydrostreptomycin, and we have found that the new compound, 3''-deoxystreptomycin is also active against a variety of streptomycin-resistant bacteria. Thus, we have accomplished this invention.

DETAILED DESCRIPTION OF THE INVENTION

According to a first aspect of this invention, therefore, there is provided as a new compound 3''-deoxystreptomycin represented by the formula

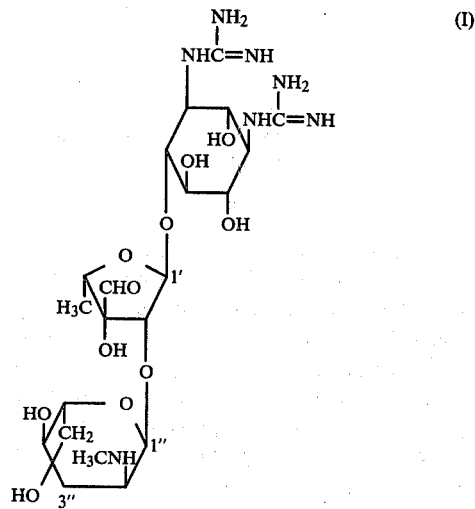

or a pharmaceutically acceptable acid-addition salt thereof.

The pharmaceutically acceptable acid-addition salt of the new compound of the above formula (I) includes a salt of 3''-deoxystreptomycin with an ordinary, non-toxic acid such as an inorganic acid, for example, hydrochloric acid, sulfuric acid, phosphoric acid, carbonic acid and the like, as well as an organic acid, for example, acetic acid, citric acid and the like.

3''-Deoxystreptomycin hydrochloride according to this invention is in the form of a colorless, solid substance which shows a specific optical rotation $[\alpha]_D^{25} -72°$ (c 1, water) but shows no definite melting point.

The antibacterial activity of 3''-deoxystreptomycin of this invention is demonstrated in Table 1 below, which exhibits the minimum inhibitory concentrations (mcg/ml) of 3''-deoxystreptomycin against various bacteria as estimated according to a standard serial dilution method using a nutrient agar medium as the incubation medium, the incubation being made at 37° C. for 17 hours. Minimum inhibitory concentrations (mcg/ml) of streptomycin and of the parent 3''-deoxydihydrostreptomycin were also estimated in the same manner as above for the comparison purpose and are shown in Table 1 below.

TABLE 1

| | MIC. (mcg/ml) | | |
| --- | --- | --- | --- |
| Test organism | 3''-Deoxystreptomycin | Streptomycin (comparative) | 3''-Deoxydihydrostreptomycin (comparative) |
| *Staphylococcus aureus* 209 P | 3.12 | 3.12 | 3.12 |
| *Sarcia lutea* 1001 | 1.56 | 1.56 | 3.12 |
| *Bacillus subtilis* NRRL B558 | 1.56 | 0.78 | 1.56 |
| *Salmonella typhi* T-63 | 0.78 | 25 | 3.12 |
| *Escherichia coli* K-12 | 1.56 | 1.56 | 1.56 |
| *Escherichia coli* ML 1629 | 1.56 | 100 | 3.12 |
| *Escherichra coli* ML 1630 | 3.12 | >100 | 1.56 |

TABLE 1-continued

| | MIC. (mcg/ml) | | |
|---|---|---|---|
| Test organism | 3″-Deoxystreptomycin | Streptomycin (comparative) | 3″-Deoxydihydrostreptomycin (comparative) |
| *Escherichia coli* W 677 | 1.56 | 1.56 | 1.56 |
| *Escherichia coli* JR66/W677 | 12.5 | >100 | 12.5 |
| *Escherichia coli* C600 R135 | 3.12 | 50 | 3.12 |
| *Pseudomonas aeruginosa* A3 | 6.25 | 6.25 | 12.5 |
| *Pseudomonas aeruginosa* No. 12 | 25 | 25 | 25 |
| *Mycobacterium smegmatis* 607 | 0.78 | 1.56 | 0.78 |

3″-Deoxystreptomycin of this invention can basically be produced starting from 3″-deoxydihydrostreptomycin and by oxidizing the hydroxymethyl group —CH$_2$OH at 3′-position of the 3″-deoxydihydrostreptomycin molecule into the aldehyde group —CHO while introduction of some amino-protecting groups and some hydroxyl-protecting groups as well as removal of these protective groups are performed. A process of producing 3″-deoxystreptomycin from 3″-deoxydihydrostreptomycin is described in the following.

3″-Deoxydihydrostreptomycin which is used as the starting substance is a compound represented by the formula

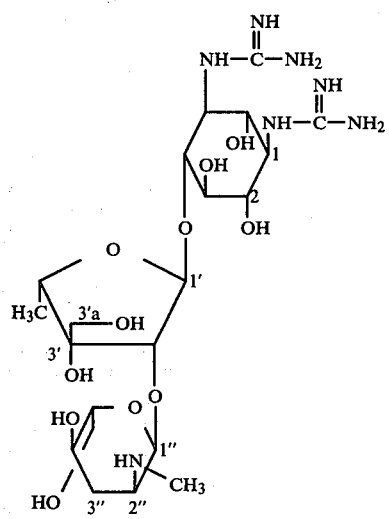

(II)

as described in the specification of the aforesaid Japanese patent application prepublication "Kokai" No. 105154/77. To synthesize 3″-deoxystreptomycin of this invention from the above-mentioned starting substance, at first, the 2″-methylamino group of 3″-deoxydihydrostreptomycin is selectively protected by a known amino-protecting group such as an aralkyloxycarbonyl group. To this end, the starting compound of the formula (II) may preferably be reacted with a 1 molar or substantially 1 molar proportion of benzyloxycarbonyl chloride in a mixture of water and acetone at a temperature of −20° to 50° C., preferably at 0° C. in the presence of a base, preferably an alkali metal carbonate such as sodium carbonate, to produce 2″-N-benzyloxycarbonyl-3″-deoxydihydrostreptomycin of the formula

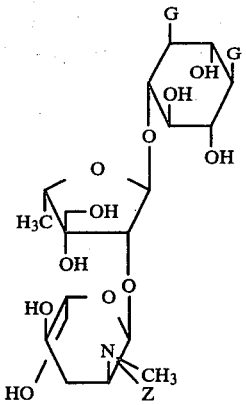

(III)

wherein G denotes a guanidyl group

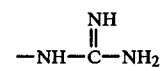

and Z denotes a benzyloxycarbonyl group —CO$_2$CH$_2$C$_6$H$_5$.

Secondly, two 3′- and 3′a-hydroxyl groups of the compound of the formula (III) are protected by a known hydroxyl-protecting group such as an alkylidene group. For this purpose, the compound of the formula (III) may preferably be reacted with a slight excess over the 1 molar proportion of 2,2-dimethoxypropane in anhydrous dimethylformamide (DMF) in the presence of a reaction catalyst such as p-toluene-sulfonic acid, whereby a pair of the two 3′- and 3′a-hydroxyl groups of the compound (III) are protected simultaneously by a single isopropylidene group, affording 2″-N-benzyloxycarbonyl-3″-deoxy-3′,3′a-O-isopropylidenedihydrostreptomycin of the formula

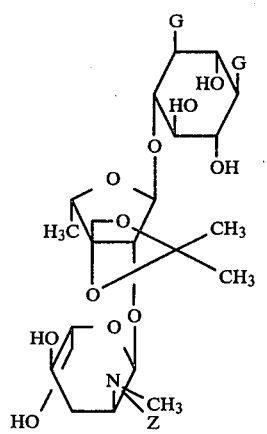

(IV)

wherein G and Z are as defined above.

Subsequently, all the remaining, free hydroxyl groups of the compound of the formula (IV) are protected by known hydroxyl-protecting group such as an alkanoyl group. To this end, all these remaining hydroxyl groups may preferably be blocked by acetyl groups. The acetylation reagent available for this purpose may be acetic anhydride as used in the presence of p-toluenesulfonic acid as a reaction catalyst. Thus, when the compound of the formula (IV) is reacted with a slight excess over the 5 molar proportion of acetic anhydride in the presence of p-toluenesulfonic acid, there is produced 2,5,6,4",6"-penta-O-acetyl-2"-N-benzyloxycarbonyl-3"-deoxy-3',3'a-O-isopropylidenedihydrostreptomycin of the formula

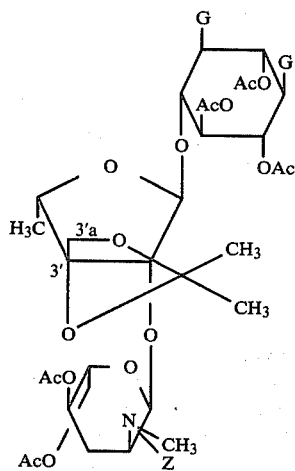

(V)

wherein G and Z have the same meaning as defined above and Ac denotes an acetyl group.

Further, the N,O-protected 3"-deoxydihydrostreptomycin compound of the formula (V) is treated so as to remove the isopropylidene group therefrom and to liberate the free hydroxyl groups at the 3'- and 3'a-positions of the compound (V). To this end, a conventional method for removing the isopropylidene group can be applied to, and for instance, the N,O-protected compound (V) may be hydrolyzed in an aqueous solution of acetic acid. There is thus formed 2,5,6,4",6"-penta-O-acetyl-2"-N-benzyloxycarbonyl-3"-deoxydihydrostreptomycin of the formula

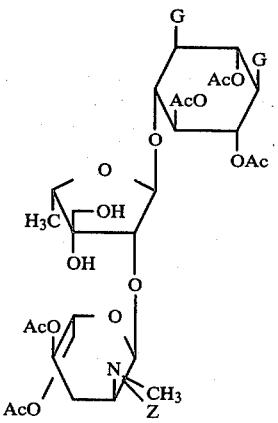

(VI)

wherein G, Z and Ac have the same meanings as defined above.

Next, the compound of the formula (VI) is treated so as to oxidize the 3'-hydroxymethyl group —CH$_2$OH (methylol group) into the aldehyde group —CHO. To this end, the compound of the formula (VI) may preferably be reacted with dimethylsulfoxide as an oxidation reagent in the presence of pyridine and trifluoroacetic acid as well as dicyclohexylcarbodiimide, whereby there is produced 2,5,6,4",6"-penta-O-acetyl-2"-N-benzyloxycarbonyl-3"-deoxystreptomycin of the formula

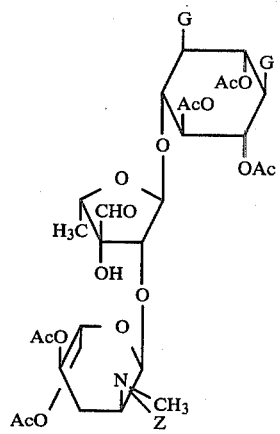

(VII)

wherein Z and Ac are as defined above. Finally, the N,O-protected 3"-deoxystreptomycin derivative of the formula (VII) is subjected to known treatments for removal of the hydroxyl-ptotecting acetyl groups and for removal of the amino-protecting benzyloxycarbonyl group therefrom. To remove the acetyl groups from the aldehyde compound of the formula (VII), this aldehyde compound (VII) may conveniently be hydrolyzed by reacting it in methanol with concentrated aqueous ammonia, and there is thus produced 2"-N-benzyloxycarbonyl-3"-deoxystreptomycin. The latter compound is then treated so as to remove therefrom the amino-protecting benzyloxycarbonyl group which is still remaining at the 2"-amino group of said compound, and there is afforded 3"-deoxystreptomycin of the formula (I) as desired. For the removal of the benzyloxycarbonyl group, a conventional method for catalytic hydrogenolysis may conveniently be applied to the 2"-N-benzyloxycarbonyl-3"-deoxystreptomycin in such a manner that the latter compound is subjected to hydrogenolysis with gaseous hydrogen at room temperature in the presence of a palladium black as a known hydrogenolysis catalyst.

In the foregoing descriptions, the process of producing the compound (I) of this invention is described with reference to such a case where the benzyloxycarbonyl group, isopropylidene group and acetyl group are particularly selected as the protective groups. It will be self-evident, however, that the required N,O-protection can be achieved using such a known amino-protecting group which serves equivalently to the benzyloxycarbonyl group, as well as such known hydroxyl-protecting groups which serve equivalently to the isopropylidene group and acetyl group, respectively.

According to a second aspect of this invention, therefore, there is provided a process for the production of 3"-deoxystreptomycin, which comprises the consecutive steps of:

(a) reacting 3"-deoxydihydrostreptomycin with a 1 molar or substantially 1 molar proportion of benzyloxycarbonyl chloride in a mixture of water and acetone at a temperature of −20° C. to 50° C. in the presence of an alkali metal carbonate to produce 2"-N-benzyloxycarbonyl-3"-deoxydihydrostreptomycin, (b) reacting the 2"-N-benzyloxycarbonyl-3"-deoxydihydrostreptomycin with 2,2-dimethoxypropane to produce 2"-N-benzyloxycarbonyl-3"-deoxy-3',3'a-O-isopropylidenedihydrostreptomycin, (c) reacting the 2″-N-benzyloxycarbonyl-3″-deoxy-3′,3′a-O-isopropylidenedihydrostreptomycin with acetic anhydride to produce 2,5,6,4″,6″-penta-O-acetyl-2″-N-benzyloxycarbonyl-3″-deoxy-3′,3′a-O-isopropylidenedihydrostreptomycin, (d) hydrolysing the product compound of the above step (c) to remove the isopropylidene group therefrom and to produce 2,5,6,4″,6″-penta-O-acetyl-2″-N-benzyloxycarbonyl-3″-deoxydihydrostreptomycin, (e) oxidizing the hydroxymethyl group at the 3′-position of the product compound of the above step (d) into the aldehyde group to produce 2,5,6,4″,6″-penta-O-acetyl-2″-N-benzyloxycarbonyl-3″-deoxystreptomycin, and (f) removing the acetyl groups and the benzyloxycarbonyl group from the product compound of the above step (e) in a manner known for removal of the hydroxyl-protecting group and amino-protecting group, to produce 3″-deoxystreptomycin.

In the process of this invention as described just above, it is unexpectable that the step (a) of the present process can proceed preferentially and give 2″-N-benzyloxycarbonyl-3″-deoxydihydrostreptomycin in such a way that the 2″-methylamino group of the starting 3″-deoxydihydrostreptomycin can be benzyloxycarbonylated selectively without involving benzyloxycarbonylation of the similarly functional guanidyl groups of the starting compound. In the steps (b) and (c) of the present process, there are chosen the hydroxyl-protecting groups of different natures for the protection of the 3′- and 3′a-hydroxyl groups (by a single isopropylidene group) and for the protection of the remaining 2-, 5-, 6-, 4″- and 6″-hydroxyl groups (by acetyl groups), and this skilled selection of the particular hydroxyl-protecting groups of the different natures can render it possible to obtain the 2,5,6,4″,6″-penta-O-acetyl-2″-N-benzyloxycarbonyl-3″-deoxydihydrostreptomycin in the subsequent, hydrolysis step (d) of the present process and to treat the partially deprotected intermediate product of the hydrolysis step (d) in the further steps (e) and (f) of the present process until the desired 3″-deoxystreptomycin of the formula (I) is afforded. Accordingly, it is clear that the skilled selection of the particular amino-protecting group and the particular hydroxyl-protecting groups as well as the ingenious combination of the consecutive steps of the present process according to this invention permit 3″-deoxystreptomycin to be synthesized from 3″-deoxydihydrostreptomycin according to the present process.

The new compound of this invention, 3″-deoxystreptomycin is of a low toxicity as will be shown by the fact that when acute toxicity of 3″-deoxystreptomycin was estimated by intravenous injection of this compound in groups of mice (ICR mice, adult female, body weight 20 g.±0.5 g, six in each group), all the treated mice survived for more than 14 days after 3″-deoxystreptomycin was administered intravenously into each mouse at a dosage of 4 mg/kg (LD$_{50}$>200 mg/kg).

The new compound of this invention is effective in therapeutic treatment of bacterial infections when administered intramuscularly in a dosage range of about 100 mg to about 1000 mg per day in divided dosages three or four times a day. Generally, the new compound of this invention may be administered orally, intraperitoneally, intravenously or intramuscularly using any pharmaceutical form known in the art for such administration and in a similar manner to streptomycin and dihydrostreptomycin. Examples of pharmaceutical forms for oral administration are powders, capsules, tablets, syrup and the like. The new compound of this invention may be formulated into an aqueous injectable solution.

According to a third aspect of this invention, therefore, there is provided an antibacterial composition comprising an antibacterially effective amount of 3″-deoxystreptomycin as the active ingredient, in association with a pharmaceutically acceptable carrier for the active ingredient.

The production of the new compound according to this invention is now illustrated with reference to the following Example.

EXAMPLE 1

(a) Synthesis of 2″-N-benzyloxycarbonyl-3″-deoxydihydrostreptomycin hydrochloride 3″-Deoxydihydrostreptomycin hydrochloride (1.40 g) and anhydrous sodium carbonate (250 mg) were dissolved in a mixture of 24 ml of water and 12 ml of acetone, and to the resulting solution was added 0.36 ml of benzyloxycarbonyl chloride under ice-cooling. The admixture obtained was vigorously agitated at a temperature of 0° C. for 1 hour (for effecting the reaction for introduction of benzyloxycarbonyl group into the 2″-amino group of 3″-deoxydihydrostreptomycin). The resulting reaction solution was admixed with 24 ml of ethyl ether, followed by well shaking and allowing the admixture to separate into the organic phase (in ethyl ether) and the aqueous phase. The aqueous layer was removed and concentrated to dryness while adjusting to the concentrated solution to a pH of about 7 by addition of hydrochloric acid.

The residue so obtained was extracted with about 70 ml of hot ethanol and the resultant ethanolic solution was concentrated to dryness. The solid obtained (1.50 g) was taken up into a small volume of water, and the resulting aqueous solution was passed through a column of 150 ml of an ion-exchange resin, Dowex 1×2 (200~400 meshes, Cl$^-$ form, a product of Dow Chemical Co., U.S.A.) using water as the development solvent. The eluate from the resin column was collected in 10 ml-fractions, and the fractions Nos. 15 to 30 which were positive to the reaction with diacetyl were combined together and concentrated to dryness to afford 1.24 g of the above titled compound in the form of its dihydrochloride. Yield 78%. $[\alpha]_D^{20} -68°$ (c 1, H$_2$O).

(b) Synthesis of 2″-N-benzyloxycarbonyl-3″-deoxy-3′,3′a-O-isopropylidenedihydrostreptomycin The product (the di-hydrochloride) (1.20 g) of the above procedure (a) of this Example was dissolved in 15 ml of anhydrous DMF (dimethylformamide) to which were then added 35 mg of p-toluenesulfonic acid and 1.2 ml of 2,2-dimethoxypropane. The admixture obtained was heated at 40° C. for 3 hours (for effecting the reaction for introduction of the 3′,3′a-O-isopropylidene group). The reaction solution was admixed with 0.4 ml of triethylamine and concentrated to a syrup which was then admixed with a volume of ethyl ether to deposit a solid. This solid (comprising the mono-O-isopropylidenated product and some poly-O-isopropylidenated products) was well washed with ethyl ether and the washed solid (1.41 g) was dissolved in 20 ml of a mixture of acetic acid and methanol (1:4 by volume). The resulting solution was heated at 50° C. for 4 hours (for effecting the hydrolytic conversion of the poly-O-isopropylidenated products into the mono-O-isopropylidenated product, namely the desired title compound). The reaction solution obtained was concentrated to a syrup, which was then admixed with a volume of acetone to deposit a solid (comprising a crude product of the title compound).

The solid so obtained (1.14 g) was then subjected to a column chromatography on cellulose (200 g, available as a tradename "Avicel", for chromatographic use) developed with pyridine-ethyl acetate-10% aqueous acetic acid (2:2:1 by volume), and the eluate from the cellulose column was collected in 50 ml-fractions. The fractions Nos. 50 to 80 containing the title compound were combined together and concentrated to dryness. The resultant solid (0.66 g) was dissolved in water and the aqueous solution obtained was passed through a column of 200 ml of an ion-exchange resin, Dowex 1×2 (200~400 meshes, Cl⁻ form) using water as the development solvent. The eluate from the resin column was collected in 10 ml-fractions, and the fractions Nos. 15 to 25 containing the title compound were combined together and concentrated to dryness to afford 640 mg of hydrochloride of the title compound. Yield 51%. $[\alpha]_D^{20} -70°$ (c 1, H$_2$O).

(c) Synthesis of 2,5,6,4'',6''-penta-O-acetyl-2''-N-benzyloxycarbonyl-3''-deoxy-3',3'a-O-isopropylidenedihydrostreptomycin The product (the hydrochloride) (840 mg) of the above procedure (b) of this Example was suspended in 16 ml of acetic anhydride, to which was then added 200 mg of p-toluenesulfonic acid. The admixture obtained was heated at 50° C. for 16 hours, and during this heating the reaction solution turned to a homogeneous solution, when the reaction for introduction of acetyl groups took place. The reaction solution was admixed with 100 mg of sodium hydrogen carbonate and then concentrated to a small volume. The concentrated solution was admixed with a volume of hexane to deposit a solid. This solid was well washed with a mixture of ethyl ether and hexane (1:3) and then dissolved in a volume of chloroform. The resulting solution in chloroform was washed with saturated aqueous sodium chloride, then dried over anhydrous sodium sulfate and concentrated to dryness. The resultant solid (1.10 g) was taken up into a volume of a mixture of water and methanol (1:4), and the solution obtained was passed through a column of 50 ml of an ion-exchange resin, Dowex 1×2 (200~400 meshes, Cl⁻ form) using the same mixture of water-methanol (1:4) as the development solvent. The eluate from the resin column was collected in 10 ml-fractions and the fractions Nos. 7 to 12 containing the above titled compound were combined together and concentrated to dryness. The solid residue was dissolved in chloroform and then reprecipitated from the chloroform solution by addition of hexane thereto, affording 910 mg of hydrochloride of the title compound. Yield 86%. $[\alpha]_D^{20} -57°$ (c 1, acetone).

(d) Synthesis of 2,5,6,4'',6''-penta-O-acetyl-2''-N-benzyloxycarbonyl-3''-deoxydihydrostreptomycin The product (the hydrochloride) (510 mg) of the above procedure (c) of this Example was dissolved in 10 ml of 75% aqueous acetic acid (a mixture of 75% acetic acid and 25% water by weight), and the resulting solution was heated at 55° C. for 4.5 hours (for effecting the reaction for removal of the isopropylidene group). The reaction solution was admixed with a volume of toluene and the admixture obtained was concentrated to dryness with azeotropically distilling off the toluene. The solid residue obtained was dissolved in a volume of methanol and then reprecipitated from the methanolic solution by addition of ethyl ether thereto. The solid obtained (470 mg) was dissolved in a mixture of water and methanol (1:3) and the resultant solution was passed through a column of 50 ml of an ion-exchange resin, Dowex 1×2 (200-400 meshes, Cl⁻ form) using the mixture of water and methanol (1:3) as the development solvent. The eluate from the resin column was collected in 10 ml-fractions, and the fractions Nos. 6 to 10 containing the above titled compound were combined together and concentrated to dryness. The solid residue was dissolved in a volume of methanol and reprecipitated from the methanolic solution by addition of ethyl ether thereto. The reprecipitated solid was removed by filtration and well washed with ethyl ether to afford 380 mg of hydrochloride of the title compound. Yield 77%. $[\alpha]_D^{20} -63°$ (c 1, acetone).

(e) Synthesis of 2''-N-benzyloxycarbonyl-3''-deoxystreptomycin

The product (the hydrochloride) (490 mg) obtained in the above procedure (d) of this Example was dissolved in 2.5 ml of anhydrous dimethylsulfoxide (DMSO) (serving as an oxidation reagent and also serving as the reaction medium), to which were then added 0.17 ml of pyridine and 0.08 ml of trifluoroacetic acid. The solution obtained was admixed with a solution of 600 mg of dicyclohexylcarbodiimide in 3 ml of anhydrous DMSO, followed by agitating the resultant admixture for 2 hours at ambient temperature (for effecting the oxidation reaction of the hydroxymethyl group). The solid as formed (comprising N,N'-dicyclohexyl urea) was removed from the reaction solution by filtration and the filtrate was well mixed with ethyl ether (about 20 ml) under shaking. This mixture obtained was left and so separated into the upper layer and the lower layer. The lower liquid layer was removed by decantation and then well washed with ethyl ether by agitating the admixture of said lower liquid layer and the ethyl ether. This admixture was allowed to stand so that it was separated into the upper phase and the lower phase. This lower liquid phase was concentrated, and the residue was taken up into about 40 ml of chloroform and the resultant solution in chloroform was washed with saturated aqueous sodium chloride (about 10 ml), and the solution phase in chloroform was separated from the aqueous phase, dried over anhydrous sodium sulfate and concentrated to dryness to leave a brown colored solid. This solid (485 mg) was dissolved in a mixture (20 ml) of concentrated aqueous ammonia and methanol (1:14) and the resultant mixture was allowed to stand for 3 hours at ambient temperature (for effecting the reaction for removal of the acetyl groups). The reaction solution was concentrated to dryness and the residue (370 mg) was taken up into water (2 ml). The solution obtained was filtered to remove the insoluble matters (about 40 mg, comprising N,N'-dicyclohexyl urea) therefrom. The filtrate was subjected to a column chromatography on Dowex 1×2 resin (30 ml, 200~400 meshes, Cl⁻ form) using water as the development solvent. The eluate from the resin column was collected in 5 ml-fractions and the fractions Nos. 4 to 8 containing the above titled compound (which gave a single spot at Rf 0.6 on a cellulose thin layer chromatography developed with butanol-pyridine-water-acetic acid (6:4:3:1)) were combined together, neutralized by addition of 0.1 N hydrochloric acid and then concentrated to a small volume. The concentrated solution obtained was adjusted to a pH of about 4 by addition of 0.1 N hydrochloric acid and then admixed with a volume of acetone to deposit a solid. The solid obtained was well washed with acetone to afford 84 mg of hydrochloride of the title compound. Yield 21%. $[\alpha]_D^{28} -64°$ (c 1, $H_2O$).

(f) Production of 3″-deoxystreptomycin

The product (the hydrochloride) (80 mg) obtained in the above procedure (e) of this Example was dissolved in 2 ml of water, to which was then added about 0.1 ml of Raney nickel (R-100, a product of Nikko Rika Kagaku Sangyo Co., Japan) (for removal of certain undesired impurities). The admixture was well shaken and mixed and then filtered to remove the Raney nickel. The Raney nickel was well washed with water and the aqueous washings were combined with the filtrate. The aqueous solution so obtained was adjusted to a pH of about 4 by addition of acetic acid and then subjected to catalytic hydrogenolysis with hydrogen at a hydrogen pressure of 3 kg/cm² for 1 hour in the presence of about 0.3 ml of palladium black with using a Parr apparatus to effect the reaction for removal of the benzyloxycarbonyl group. The reaction solution was filtered to remove the palladium black therefrom, and the filtrate was concentrated to dryness. The solid obtained (65 mg) was dissolved in a small volume of water, and the resulting aqueous solution was subjected to a column chromatography on Dowex 1×2 resin (10 ml, 200~400 meshes, $Cl^-$ form) using water as the development solvent. The eluate from the resion column was collected in 1 ml-fractions, and the fractions Nos. 7 to 12 containing the desired 3″-deoxystreptomycin were combined together and concentrated to dryness to afford 53 mg of hydrochloride of the titled compound. Yield 75%. $[\alpha]_D^{25} -72°$ (c 1, $H_2O$).

What we claim is:

1. 3″-Deoxystreptomycin represented by the formula

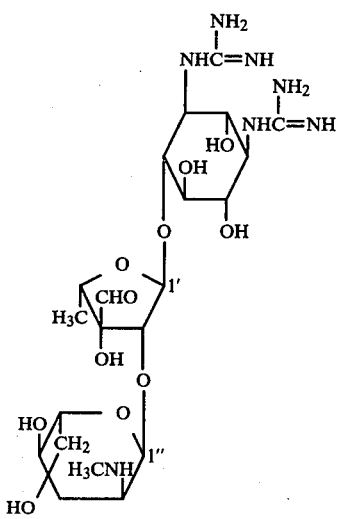

and a pharmaceutically acceptable acid-addition salt thereof.

2. A process for the production of 3″-deoxystreptomycin which comprises the consecutive steps of:
(a) reacting 3″-deoxydihydrostreptomycin with a 1 molar or substantially 1 molar proportion of benzyloxycarbonyl chloride in a mixture of water and acetone at a timperature of −20° C. to 50° C. in the presence of an alkali metal carbonate to produce 2″-N-benzyloxycarbonyl-3″-deoxydihydrostreptomycin,
(b) reacting the 2″-N-benzyloxycarbonyl-3″-deoxydihydrostreptomycin with 2,2-dimethoxypropane to produce 2″-N-benzyloxycarbonyl-3″-deoxy-3′,3′a-O-isopropylidenedihydrostreptomycin,
(c) reacting the 2″-N-benxyloxycarbonyl-3″-deoxy-3′,3′a-O-isopropylidenedihydrostreptomycin with acetic anhydride to produce 2,5,6,4″,6″-penta-O-acetyl-2″-N-benzyloxycarbonyl-3″-deoxy-3′,3′a-O-isopropylidenedihydrostreptomycin,
(d) hydrolysing the product compound of step (c) with aqueous acetic acid to remove the isopropylidene group therefrom and to produce 2,5,6,4″,6″-penta-O-acetyl-2″-N-benzyloxycarbonyl-3″-deoxydihydrostreptomycin,
(e) oxidizing with dimethylsulfoxide in the presence of pyridine the hydroxymethyl group at the 3′-position of the product compound of step (d) into an aldehyde group to produce 2,5,6,4″,6″,-penta-O-acetyl-2″-N-benzyloxycarbonyl-3″-deoxystreptomycin, and
(f) removing the acetyl groups by hydrolysis with aqueous ammonia and the benzyloxycarbonyl group by catalytic hydrogenolysis from the product compound of step (e) to produce 3″-deoxystreptomycin.

3. A process as claimed in claim 2 in which the presence of p-toluenesulfonic acid is provided as a reaction catalyst in the step (b) of the process.

4. A process as claimed in claim 2 in which the presence of p-toluenesulfonic acid is provided as a reaction catalyst in the step (c) of the process.

5. A process as claimed in claim 2 in which the hydroxymethyl group at the 3′-position of 2,5,6,4″,6″-penta-O-acetyl-2″-N-benzyloxycarbonyl-3″-deoxydihydrostreptomycin is oxidized in the step (e) of the process by reacting with dimethylsulfoxide in the presence of pyridine and trifluoroacetic acid as well as dicyclohexylcarbodiimide.

6. An antibacterial composition comprising an antibacterially effective amount of 3″-deoxystreptomycin as the active ingredient, in association with a pharmaceutically acceptable carrier for the active ingredient.

7. 2,5,6,4″,6″-Penta-O-acetyl-2″-N-benzyloxycarbonyl-3″-deoxydihydrostreptomycin.

* * * * *